United States Patent
Laghi

(12) 
(10) Patent No.: US 6,663,672 B1
(45) Date of Patent: Dec. 16, 2003

(54) VARIABLE CROSS SECTION PROSTHETIC FOOT WITH CARBON SPHERES

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 0 days.

(21) Appl. No.: 10/064,848

(22) Filed: Aug. 22, 2002

(51) Int. Cl.[7] ............................... A61F 2/66; A61F 2/64
(52) U.S. Cl. ........................................... 623/55; 623/47
(58) Field of Search ............................ 623/47, 50, 52, 623/27, 53, 33, 55, 35

(56) References Cited

U.S. PATENT DOCUMENTS

| | | | | |
|---|---|---|---|---|
| 5,258,038 A | * | 11/1993 | Robinson et al. | 623/49 |
| 5,376,141 A | * | 12/1994 | Phillips | 623/55 |
| 5,549,714 A | * | 8/1996 | Phillips | 623/33 |
| 5,728,177 A | * | 3/1998 | Phillips | 623/55 |
| 5,776,205 A | * | 7/1998 | Phillips | 623/55 |
| 5,944,760 A | * | 8/1999 | Christensen | 623/55 |
| 6,071,313 A | * | 6/2000 | Phillips | 623/55 |
| 6,197,068 B1 | * | 3/2001 | Christensen | 623/55 |
| 2002/0013628 A1 | * | 1/2002 | Harris | 623/55 |

FOREIGN PATENT DOCUMENTS

WO    wo 00/71061    * 11/2000

* cited by examiner

Primary Examiner—Corrine McDermott
Assistant Examiner—Thomas J Sweet
(74) Attorney, Agent, or Firm—Ronald E. Smith; Smith & Hopen, P.A.

(57) ABSTRACT

A dynamic prosthetic foot having variable cross section density. An ankle part diverges upwardly from a sole along a transverse parting line and includes a vertical part. A longitudinally extending slot divides the vertical part into a lateral pylon support and a medial pylon support. A lateral pylon connector is secured to the lateral pylon support and a medial pylon connector is secured to the medial pylon support. A second embodiment eliminates the pylon connectors and the lateral and medial pylon supports are elongated to provide lateral and medial pylons. High rigidity areas of the foot are formed of a high strength outer layer made with carbon reinforced composite and an inner layer made of a matrix within which is dispersed a plurality of low density hollow spheres. High stress areas of the foot are formed of carbon-reinforced composite throughout.

7 Claims, 4 Drawing Sheets

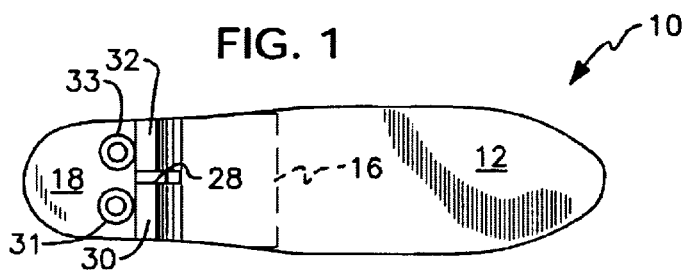
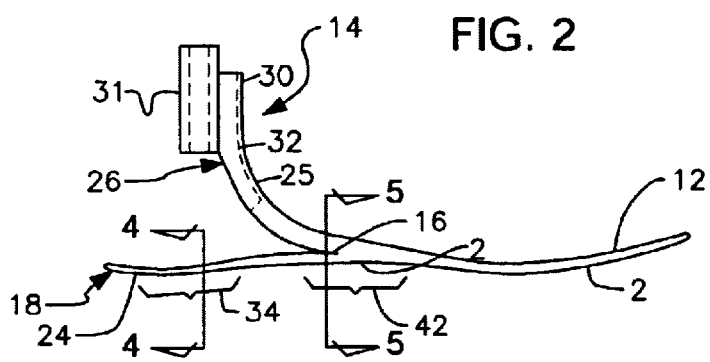
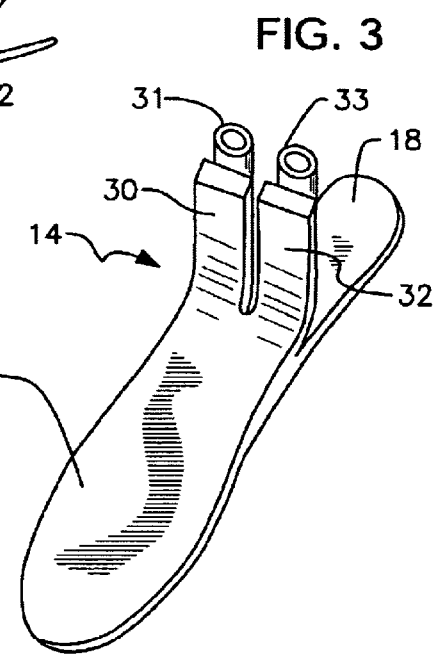
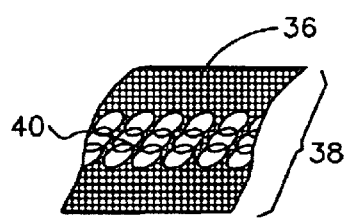
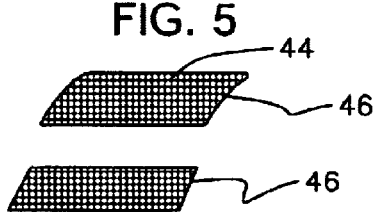

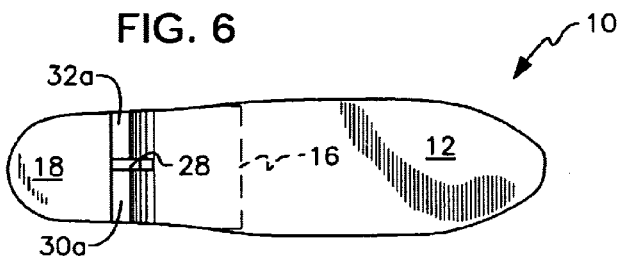
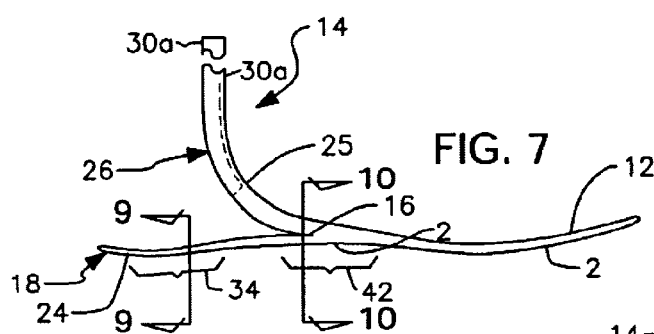
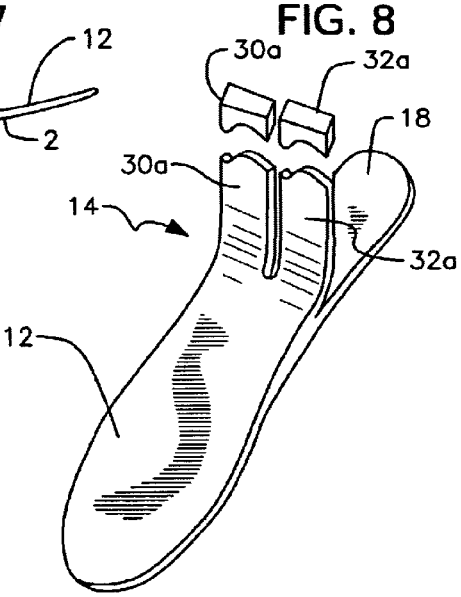
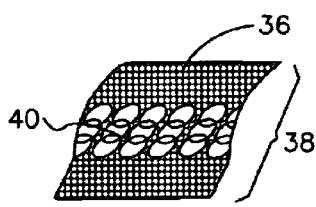
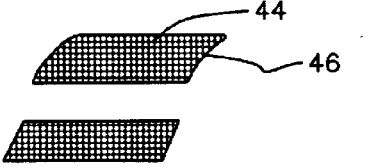

VARIABLE CROSS SECTION PROSTHETIC FOOT WITH CARBON SPHERES

BACKGROUND OF INVENTION

1. Field of the Invention

This invention relates, generally, to the art of prosthetics. More particularly, it relates to improvements in prosthetic feet.

2. Description of the Prior Art

The weight of a prosthetic foot is of paramount importance in prostheses. The foot is the component of the prosthesis that is furthest from the center of rotation ie., the knee joint.

The inertial resistance to changes of speed is directly proportional to the weight of any component but is proportional to the fourth power of the distance of any component from the center of rotation. Thus, the weight of the components that are farther away from the center of rotation is of much greater relevance than that of components that are closer to the center of rotation. For example, a reduction of one-tenth of a pound in the weight of a foot located fifteen (15) inches from a knee joint has the same effect on inertial resistance to changes in speed as a reduction of eight and one-tenths (8.1) pounds in the weight of a component five (5) inches from the knee joint.

What is needed, then, is a dynamic prosthetic foot having less weight than the dynamic prosthetic feet of the prior art.

Prosthetic feet have been made using carbon fibers in an epoxy matrix. Carbon-epoxy is a composite material with a very high strength to weight ratio, but not all sections of a prosthetic foot require the same flexural strength. Some sections are stressed much more than others. Moreover, not all sections of a prosthetic foot require the same rigidity. Some sections need to be more rigid than others and some sections need to be flexible.

Another need therefore exists for a prosthetic foot that is made with carbon reinforced composite that has a variable cross section density so that the sections thereof that require rigidity are rigid and the sections thereof requiring flexibility are flexible.

However, in view of the prior art considered as a whole at the time the present invention was made, it was not obvious to those of ordinary skill in the pertinent art how to provide a dynamic prosthetic foot having variable cross section density.

SUMMARY OF INVENTION

The long-standing but heretofore unfulfilled need for an improved dynamic prosthetic foot is now met by a new, useful, and nonobvious dynamic prosthetic foot that is light-in-weight and that is made with a carbon reinforced composite having a variable cross section density.

The novel prosthetic foot includes a sole having an anterior, toe section and a posterior, heel section. An ankle part separates from the sole along a transverse parting line and includes a gradual upward bend and a vertically extending part.

A longitudinally extending slot divides the ankle part into a lateral pylon support and a medial pylon support. A lateral pylon connector is secured in trailing relation to the lateral pylon support and a medial pylon connector is secured in trailing relation to the medial pylon support.

The lateral pylon support has a greater thickness and thus less resiliency than the medial pylon support so that externally imparted forces appearing on the lateral pylon support are transferred at least in part to the medial pylon support whereby a sound leg may oppose the transferred forces.

A first convexity is formed in the sole and is adapted to perform a function like that of a ball of a natural foot. A second convexity is formed in the heel section, and said second convexity is adapted to perform a function like a bottom of a heel of a natural foot. A concavity is formed in the sole between the first and second concavities, and is adapted to perform a function like an arch of a natural foot.

In a second embodiment, the pylon connectors are eliminated and the lateral and medial pylon supports are elongated so that they become lateral and medial pylons, respectively. They are about twenty inches (20") in length and are cut to length as required by a prosthetist when the novel foot is secured to a prosthetic socket.

The sole in the region of the first convexity is formed of a high strength outer layer made with carbon reinforced composite and an inner layer made of a matrix within which is dispersed a plurality of low density hollow spheres. The sole in the region of the concavity is formed of carbon-reinforced composite throughout.

An important object of this invention is to provide a prosthetic foot made with carbon reinforced composite having a variable cross section density.

A more specific object is to provide a prosthetic foot where the sections of the foot that are subjected to high stress, such as the ankle and the anterior section, are formed of carbon-reinforced composite throughout their entire cross section.

Another specific object is to provide a prosthetic foot where the sections of the foot that are not required to flex and that require high rigidity, such as part of the sole, the shin, and the upper part of the foot have a structure that includes a high strength outer layer made of carbon reinforced composite and an inner layer made in a matrix structure dispersed with low density hollow spheres such as carbon spheres or acrylonitrile spheres.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a top plan view of a prosthetic foot with variable cross section density;

FIG. 2 is a side elevational view thereof;

FIG. 3 is a perspective view thereof;

FIG. 4 is a sectional view taken along line 4—4 in FIG. 2;

FIG. 5 is a sectional view taken along line 5—5 in FIG. 2;

FIG. 6 is a top plan view of a second embodiment of the prosthetic foot;

FIG. 7 is a side elevational view of said second embodiment;

FIG. 8 is a perspective view of said second embodiment;

FIG. 9 is a sectional view of said second embodiment taken along line 9—9 in FIG. 8;

FIG. 10 is a sectional view taken along line 10—10 in FIG. 8 of said second embodiment;

DETAILED DESCRIPTION

Figure 11:
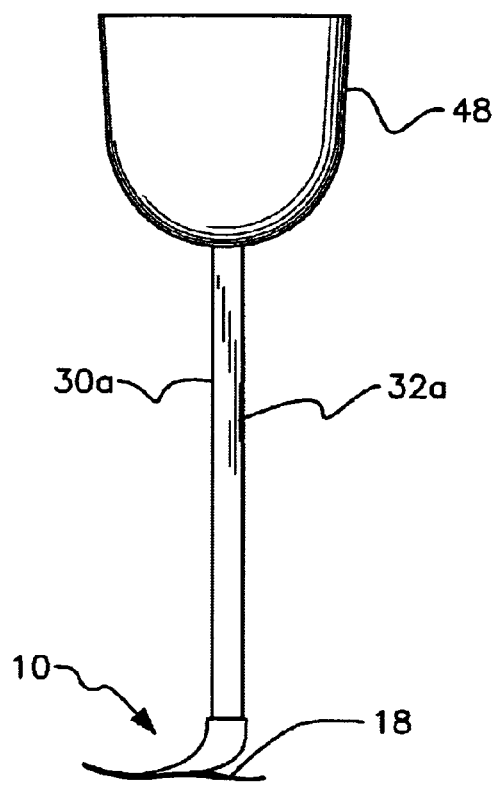
FIG. 11 is a perspective view of the elongate pylons embodiment when attached to a socket.

Referring to FIGS. 1–3, it will there be seen that the reference numeral 10 denotes an illustrative embodiment of the novel dynamic prosthetic foot.

Prosthetic foot 10 includes a sole 12, an ankle part 14 that separates from sole 12 at transverse parting line 16, and a heel 18 that is formed integrally and is substantially coplanar with sole 12. Transverse parting line 16 is about mid-length of foot 10, being a little closer to the heel/posterior end thereof than the toe/anterior end thereof.

Concavity 20 is formed about mid-length of sole 12 and performs a function corresponding to the arch of a natural foot. Convexity 22 is formed about mid-way between concavity 20 and the toe end of foot 10 and performs a function corresponding to the ball of a natural foot. Second convexity 24 is formed in heel 18 and performs a function corresponding to the bottom of a heel of a natural foot.

Ankle part 14 includes a first upwardly-turned (with respect to sole 12) gradual bend 25 and vertically extending part 26.

A longitudinally extending slot 28 divides vertically extending part 26 into lateral pylon support 30 and medial lateral support 32. Slot 28 extends from a free end of ankle part 14 to a preselected point slightly anterior to vertically extending part 26.

Lateral pylon connector 31 is secured by suitable means to a trailing side of lateral pylon connector 30 and medial pylon connector 33 is secured by suitable means to a trailing side of medial pylon connector 32.

Lateral pylon support 30 is a little thicker and thus less flexible than medial pylon connector 32 as indicated in all FIGS. 1–3, with the desirable result that externally imparted forces are transferred from the lateral side of prosthetic foot 10 to the medial side thereof as is the case in a natural foot. This directs such forces toward the natural leg of the prosthetic foot user.

Bracketed area 34 in FIG. 2 is a high rigidity area because it is not required to flex. This area is preferably made of a high strength outer layer made of carbon reinforced composite such as carbon yarn 36 (FIG. 4) and an inner layer made of a matrix 38 that is dispersed with low-density hollow spheres 40 such as carbon spheres or acrylonitrile spheres. Others areas of foot 10, such as part of sole 12 and ankle 14 may also be formed of such carbon yarn 36, matrix 38, and hollow spheres 40.

Bracketed area 42 in FIG. 2 is a high stress area. It is preferably made of a carbon reinforced composite throughout, such as a carbon yarn 44 (FIG. 5) in epoxy matrices 46. Other areas of foot 10, such as ankle part 14 and the anterior part of sole 12 may also be formed of such carbon reinforced composite.

FIGS. 6–10 depict a second embodiment where pylon connectors 31, 33 are eliminated and where pylon supports 30, 32 are elongated into lateral pylon 30a and medial pylon 32a, respectively. Pylon supports 30a, 32a are about twenty inches (20") in length and are cut to size as needed by a prosthetist when securing the uppermost ends of said pylons to a prosthetic socket.

FIG. 11 depicts the novel structure when equipped with elongate pylons 30a, 32a and when the respective uppermost ends of said pylons have been secured to prosthetic socket 48.

After pylons 30a, 32a have been cut to a desired length, a prosthetist has several options by which the pylons may be connected to prosthetic socket 48. Pylons 30a, 32a may be laminated into prosthetic socket 48 as illustrated in said FIG. 11. This forms a permanent connection between pylons 30a, 32a and socket 48.

Figure 12:
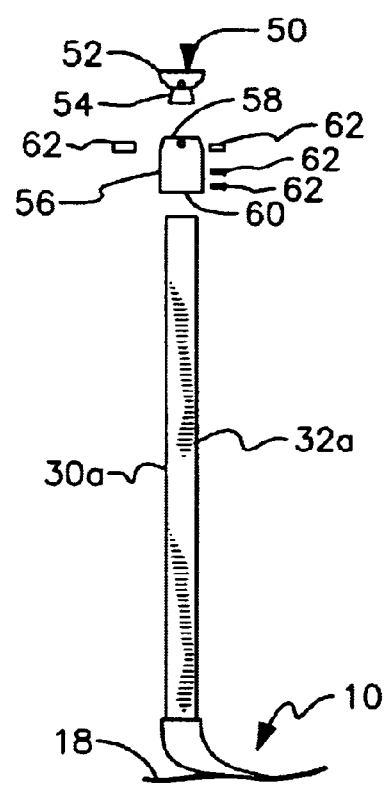
FIG. 12 is a perspective view of the elongate pylons embodiment and further depicting connector means, in exploded form, for connecting said elongate pylons to a socket.

A second option includes the use of a commercially available pyramid connector 50 as depicted in FIG. 12. Such pyramid connectors have been in use for fifty or so years. Pyramid connector 50 includes upper part 52 and lower part 54 that depends from the upper part. Upper part 52 is attached to the lowermost or distal end of socket 48. A hollow pyramid-receiving connector 56 has an open upper end 58 that receives lower part 54 of pyramid connector 50 and an open lower end 60 that receives the respective uppermost ends of pylons 30a, 32a. Lower end 54 of pyramid connector 50 and the respective upper ends of pylons 30a, 32a are captured in said hollow pyramid-receiving connector 56 by a plurality of set screws and other suitable fastening means, collectively denoted 62. Pyramid connector 50 and pyramid-receiving connector 56 are employed to enable adjustment of the angle of pylons 30a, 32a so that prosthetic foot 10 falls in the correct medial/lateral and anterior/posterior planes, as perhaps best understood by making reference to FIGS. 11 and 12.

A third option available to the prosthetist after cutting pylons 30a, 32a to their correct length is to laminate the pylons to an unillustrated comporient and to attach that component to the socket.

Figure 13A:
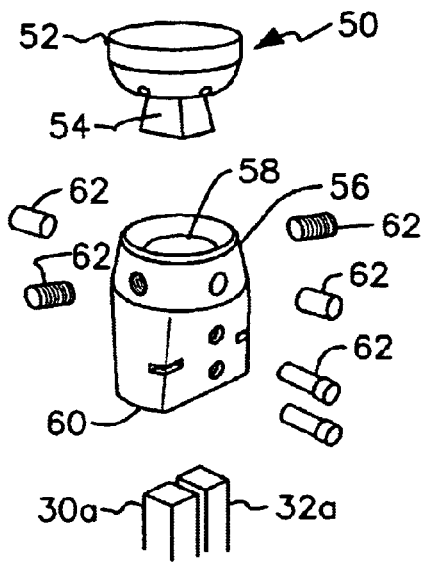
FIG. 13A is an exploded first perspective view of said connector means.
Figure 13B:
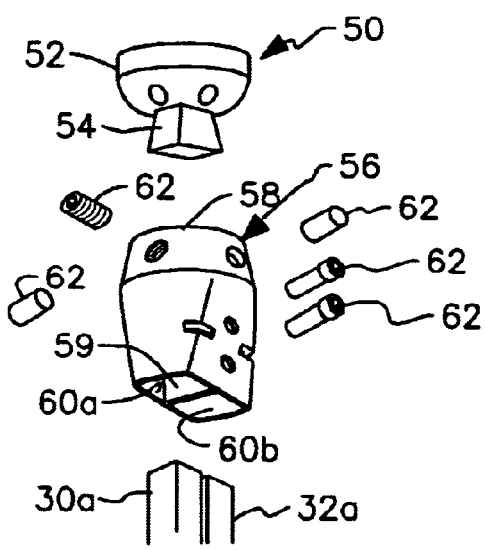
FIG. 13B is an exploded second perspective view of said connector means.
Figure 13C:
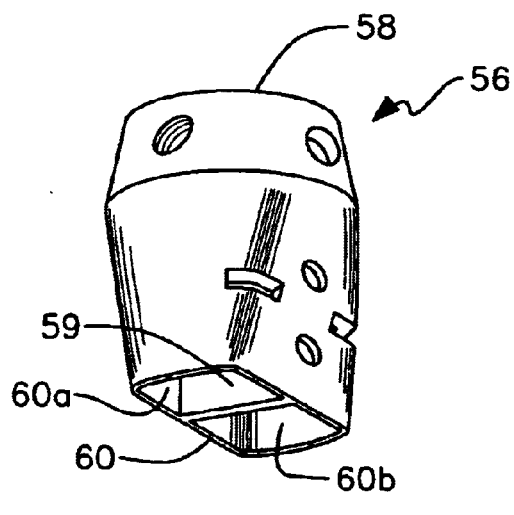
FIG. 13C is a first perspective view of a pyramid-receiving connector.
Figure 13D:
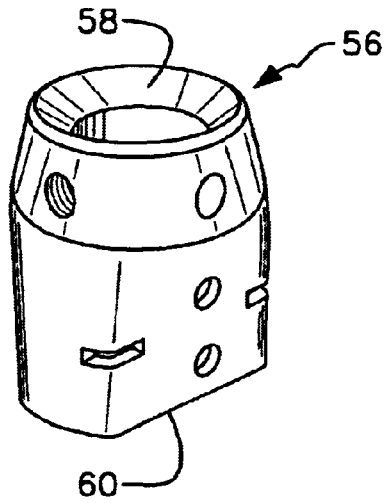
FIG. 13D is a second perspective view of said pyramid-receiving connector.

FIGS. 13A and 13B provide a more detailed perspective view of pyramid connector 50 and pyramid-receiving connector 56. FIGS. 13C and 13D provide a more detailed perspective view of pyramid-receiving connector 56. Partition wall 59 divides open lower end 60 of pyramid-receiving connector 56 into compartments 60a, 60b for receiving pylons 30a, 32a, respectively.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A dynamic prosthetic foot, comprising:

a sole having an anterior, toe section and a posterior, heel section;

an ankle part that separates from said sole along a transverse parting line;

said ankle part including a gradual upward bend and a vertically extending part;

a longitudinally extending slot that divides said vertically extending part into a lateral pylon support and a medial pylon support;

a concavity formed in said sole about mid-way between said heel and toe of said dynamic prosthetic foot, said concavity adapted to function like an arch of a natural foot;

a first convexity formed in said sole between said first concavity and a toe end of said dynamic prosthetic foot, said first convexity adapted to function like a ball of a natural foot;

a second convexity formed in said heel section, said second convexity adapted to function like a bottom of a heel of a natural foot;

said sole in the region of said second convexity being formed of a high strength outer layer made with carbon reinforced composite and an inner layer made of a matrix within which is dispersed a plurality of low density hollow spheres;

said sole in the region of said concavity being formed of carbon-reinforced composite throughout;

a lateral pylon connector, adapted for connection to a lateral pylon, secured to a trailing side of said lateral pylon support and a medial pylon connector, adapted for connection to a medial pylon, secured to a trailing side of said medial pylon support;

said lateral pylon support having a greater thickness and thus less resiliency than said medial pylon support so that externally imparted forces appearing on said lateral pylon support are transferred at least in part to said medial pylon support whereby a sound leg may oppose said transferred forces.

2. The dynamic prosthetic foot of claim 1, wherein said transverse parting line is approximately half way between a toe end of said sole and a heel end of said sole.

3. A dynamic prosthetic foot, comprising:

a sole having an anterior, toe section and a posterior, heel section;

an ankle part that separates from said sole along a transverse parting line;

said ankle part including a gradual upward bend and a vertically extending part;

a longitudinally extending slot that divides said vertically extending part into a lateral pylon and a medial pylon;

a concavity formed in said sole about mid-way between said heel and toe of said dynamic prosthetic foot, said concavity adapted to function like an arch of a natural foot;

a first convexity formed in said sole between said first concavity and a toe end of said dynamic prosthetic foot, said first convexity adapted to function like a ball of a natural foot;

a second convexity formed in said heel section, said second convexity adapted to function like a bottom of a heel of a natural foot;

said sole in the region of said second convexity being formed of a high strength outer layer made with carbon reinforced composite and an inner layer made of a matrix within which is dispersed a plurality of low density hollow spheres;

said sole in the region of said concavity being formed of carbon-reinforced composite throughout;

said lateral pylon having a greater thickness and thus less resiliency than said medial pylon so that externally imparted forces appearing on said lateral pylon are transferred at least in part to said medial pylon whereby a sound leg may oppose said transferred forces.

4. The dynamic prosthetic foot of claim 3, wherein said transverse parting line is approximately half way between a toe end of said sole and a heel end of said sole.

5. The dynamic prosthetic foot of claim 3, wherein said lateral and medial pylons are laminated at respective uppermost ends thereof to a prosthetic socket.

6. The dynamic prosthetic foot of claim 3, wherein said lateral and medial pylons are connected at respective uppermost ends thereof to a connector member and wherein said connector member is laminated to a prosthetic socket.

7. The dynamic prosthetic foot of claim 6, wherein said lateral and medial pylons are connected at respective uppermost ends thereof to a pyramid-receiving connector that engages a pyramid that depends from said prosthetic socket.

* * * * *